(12) United States Patent
Lee et al.

(10) Patent No.: US 7,637,147 B2
(45) Date of Patent: Dec. 29, 2009

(54) ULTRAHIGH-PRESSURE DUAL ON-LINE SOLID PHASE EXTRACTION/CAPILLARY REVERSE-PHASE LIQUID CHROMATOGRAPHY SYSTEM

(75) Inventors: Sang Won Lee, Seoul (KR); Seok Won Hyung, Hamyang-gun (KR)

(73) Assignee: Korea University Industry and Academy Cooperation Foundation, Seoul (KR)

( * ) Notice: Subject to any disclaimer, the term of this patent is extended or adjusted under 35 U.S.C. 154(b) by 210 days.

(21) Appl. No.: 11/934,029

(22) Filed: Nov. 1, 2007

(65) Prior Publication Data

US 2008/0115568 A1 May 22, 2008

(30) Foreign Application Priority Data

Nov. 16, 2006 (KR) .................. 10-2006-0113175

(51) Int. Cl.
*G01N 30/00* (2006.01)
(52) U.S. Cl. ..................................... 73/61.56
(58) Field of Classification Search ............. 73/61.52, 73/61.55, 61.56, 61.59
See application file for complete search history.

(56) References Cited

U.S. PATENT DOCUMENTS

| | | | |
|---|---|---|---|
| 4,271,697 A * | 6/1981 | Mowery, Jr. ............. | 73/61.52 |
| 5,135,718 A * | 8/1992 | Kawaguchi et al. ....... | 422/70 |
| 2005/0136458 A1* | 6/2005 | Dale et al. ............. | 435/6 |
| 2005/0218055 A1* | 10/2005 | Hayashi et al. .......... | 210/198.2 |
| 2006/0219638 A1* | 10/2006 | Watanabe et al. ........ | 210/656 |
| 2007/0000838 A1* | 1/2007 | Shih et al. ............. | 210/656 |
| 2008/0209983 A1* | 9/2008 | Sasano et al. ........... | 73/23.41 |

OTHER PUBLICATIONS

Link, A., et al., *Direct analysis of protein complexes using mass spectrometry*, Nature Biotechnology, vol. 17, Jul. 1999, pp. 676-682.

(Continued)

*Primary Examiner*—John Fitzgerald
(74) *Attorney, Agent, or Firm*—Christie, Parker & Hale, LLP

(57) ABSTRACT

An ultrahigh-pressure dual on-line solid phase extraction/capillary reverse-phase liquid chromatography (DO-SPE/cR-PLC) system is provided. The system comprises: a sample loading valve into which a first solvent and a sample to be analyzed are loaded; a first column valve in flow communication with a first solid-phase extraction column and a first reverse-phase liquid chromatography column; a second column valve in flow communication with a second solid-phase extraction column and a second reverse-phase liquid chromatography column; a column-switching valve for determining whether the sample is transferred to either the first column valve or the second column valve; a solvent selection valve in flow communication with the first and second column valves to supply the first solvent or a mixed solvent of the first solvent and a second solvent to the first and second column valves; a second solvent loading valve, in flow communication with a solvent mixer, into which the first and second solvents are loaded; a supply pump for loading the second solvent into the second solvent loading valve; and a supply pump for loading the first solvent into the sample loading valve, the second solvent loading valve and the solvent selection valve. The system requires minimal time (i.e. dead time) for column equilibration between successive experiments to shorten the total time required for the experiments by a factor of about two. In addition, the system enables rapid sample injection, on-line sample desalting and sample enrichment. Furthermore, the system is highly reproducible in terms of liquid chromatography (LC) retention time and can be operated at a pressure as high as 10,000 psi.

16 Claims, 11 Drawing Sheets

OTHER PUBLICATIONS

Chen, E., et al., *Large Scale Protein Profiling by Combination of Protein Fractionation and Multidimensional Protein Identification Technology (MudPIT)*, Molecular & Cellular Proteomics, 5.1, (2006), pp. 53-56.

Kim M., et al., *Development of Ultra-High Pressure Capillary Reverse-Phase Liquid Chromatography/Tandem Mass Spectrometry for High-Sensitive and High-Throughput Proteomics*, Bull. Korean Chem. Soc., vol. 25, No. 12, (2004), pp. 1833-1839.

Shen, Y., et al., *High-Efficiency On-Line Solid-Phase Extraction Coupling to 15-150-μm-i.d. Column Liquid Chromatography for Proteomic Analysis*, Anal. Chem., vol. 75, (2003), pp. 3596-3605.

Shen, Y., et al., *Ultrasensitive Proteomics Using High-Efficiency On-Line Micro-SPE-NanoLC-NanoESI MS and MS/MS*, Anal. Chem., vol. 76, (2004), pp. 144-154.

Shen, Y., et al., *Ultrahigh-Throughput Proteomics Using Fast RPLC Separations with ESI-MS/MS*, Anal. Chem., vol. 77 (2005), pp. 6692-6701.

* cited by examiner

Time(min)

Start time = 3 hrs
First Column used

Start time = 6 hrs
Second Column used

US 7,637,147 B2

ULTRAHIGH-PRESSURE DUAL ON-LINE SOLID PHASE EXTRACTION/CAPILLARY REVERSE-PHASE LIQUID CHROMATOGRAPHY SYSTEM

BACKGROUND OF THE INVENTION

1. Field of the Invention

The present invention relates to an ultrahigh-pressure dual on-line solid phase extraction/capillary reverse-phase liquid chromatography system (hereinafter, abbreviated as a 'DO-SPE/cRPLC system' and also referred to simply as a 'system'. More specifically, the present invention relates to an ultrahigh-pressure DO-SPE/cRPLC system that requires minimal time (i.e. dead time) for column equilibration between successive experiments to shorten the total time required for the experiments by a factor of about two, that enables rapid sample injection, on-line sample desalting and sample enrichment, that is highly reproducible in terms of liquid chromatography (LC) retention time, and that can be operated at a pressure as high as 10,000 psi.

2. Description of the Related Art

On-line solid phase extraction/capillary reverse-phase liquid chromatography is recognized as one of the most powerful analytical tools for current proteomic research due to its high analysis efficiency. On-line solid phase extraction/capillary reverse-phase liquid chromatography has various advantages, and particularly, the ability to effectively separate trace amounts of biological analytes and the wide analyte-solid phase interaction range enable researchers to identify low-abundance proteins with great efficiency.

Mass spectrometry (MS)-based methods for identifications of proteins have become standard analytical platforms in proteomic research. The shotgun approach, or bottom-up approach, which is among the most well-established and robust MS-based strategies, relies on proteolytic digestion of proteins into peptides prior to analysis using a mass spectrometer. Such digestion of proteins increases the solubility of the biological samples and creates peptide fragments that are readily ionized and detected in the mass spectrometer.

This process, however, inevitably results in increased sample complexity. For example, yeast proteome, which—at ca. 6,000 different proteins—is one of the simpler proteomes, will provide over 300,000 peptides. Among the various approaches to overcoming this problem is the use of multidimensional protein identification technology (Link, A. J., Eng, J., Schieltz, D. M., Carmack, E., et al., *Nat. Biotechnol.* 1999, 17, 676-682; Chen, E. I., Hewel, J., Felding-Habermann, B., Yates, J. R. III, *Mol. Cell. Proteomics* 2006, 5, 53-56.). However, the efficiency and sensitivity of liquid chromatography (LC) columns remain to be improved significantly. It is already known that the sensitivity of liquid chromatography/mass spectrometry (LC/MS) experiments can be increased dramatically upon decreasing the inner diameters of the separation columns while maintaining their lengths constant (Kim, M.-S., Choie, W.-S., Shin, Y. S., Yu, M. H., Lee, S.-W., *Bull. Korean Chem. Soc.* 2004, 25, 1833-1839.).

In many cases (e.g., for biological samples that contain substantial amounts of detergents and salts), on-line desalting steps are essential prior to mass analyses because such impurities suppress ionization process of peptide analytes, resulting in decreased detection sensitivity of the analytes. On-line desalting is preferred to off-line methods because the latter are rather time-consuming and also inevitably suffer from sample loss.

Another practical issue when using long, small-inner diameter (ID) capillary columns packed with hydrophobic media is their extended column equilibration (or regeneration) time; in practice, 1-m-long, 75-m-ID columns require at least 2 hours of equilibration before the capillary columns can be reused in subsequent experiments.

SUMMARY OF THE INVENTION

The present invention has been made in an effort to solve the problems of the prior art, and it is an object of the present invention to provide an ultrahigh-pressure DO-SPE/cRPLC system that requires minimal time (i.e. dead time) for column equilibration between successive experiments to shorten the total time required for the experiments by a factor of about two, that enables rapid sample injection, on-line sample desalting and sample enrichment, that is highly reproducible in terms of liquid chromatography (LC) retention time, and that can be operated at a pressure as high as 10,000 psi.

In order to accomplish the above object of the present invention, there is provided an ultrahigh-pressure DO-SPE/cRPLC system comprising:

a sample loading valve into which a first solvent and a sample to be analyzed are loaded;

a first column valve in flow communication with a first solid-phase extraction column and a first reverse-phase liquid chromatography column;

a second column valve in flow communication with a second solid-phase extraction column and a second reverse-phase liquid chromatography column;

a column-switching valve for determining whether the sample is transferred to either the first column valve or the second column valve;

a solvent selection valve in flow communication with the first and second column valves to supply the first solvent or a mixed solvent of the first solvent and a second solvent to the first and second column valves;

a second solvent loading valve, in flow communication with a solvent mixer, into which the first and second solvents are loaded;

a supply pump for loading the second solvent into the second solvent loading valve; and a supply pump for loading the first solvent into the sample loading valve, the second solvent loading valve and the solvent selection valve.

In a preferred embodiment of the present invention, the sample loading valve includes a port into which the first solvent is introduced, a port into which the sample is introduced, a port through which an excess amount of the sample flows out to waste, ports to which a sample storage loop is connected, and a port to which the column-switching valve is connected.

In a further preferred embodiment of the present invention, the column-switching valve includes a port to which the sample loading valve is connected, a port to which the first column valve is connected, and a port to which the second column valve is connected.

In another preferred embodiment of the present invention, the first column valve includes a port to which the column-switching valve is connected, a port to which the first solid-phase extraction column is connected, a port to which the first reverse-phase liquid chromatography column is connected, a port to which a solvent flow splitter is connected, a port to which the solvent selection valve is connected, and a sample flow control port.

In another preferred embodiment of the present invention, the second column valve includes a port to which the column-switching valve is connected, a port to which the second solid-phase extraction column is connected, a port to which the second reverse-phase liquid chromatography column is connected, a port to which a solvent flow splitter is connected, a port to which the solvent selection valve is connected, and a sample flow control port.

In another preferred embodiment of the present invention, the solvent selection valve includes a port to which the first column valve is connected, a port to which the second column valve is connected, a port into which the first solvent is introduced, and a port into which the mixed solvent is introduced.

In another preferred embodiment of the present invention, the second solvent loading valve includes a port into which the first solvent is introduced, a port into which the second solvent is introduced, and a port to which the solvent mixer is connected.

In another preferred embodiment of the present invention, the first solvent is loaded at a pressure of 5,000 to 20,000 psi by means of the first solvent supply pump.

In another preferred embodiment of the present invention, the second solvent is loaded at a pressure of 5,000 to 20,000 psi by means of the second solvent supply pump.

In another preferred embodiment of the present invention, each of the first and second solid-phase extraction columns has a diameter of 50 to 500 μm and a length of 1 to 4 cm.

In another preferred embodiment of the present invention, the solvent flow splitter is connected to a 'T'-shaped solvent separation column to divide the solvent flow, and the solvent separation column allows the mixed solvent to flow out at a rate of 15 to 20 μl/min to generate a solvent gradient and serves to transfer only the remaining portion of the mixed solvent to the first and second column valves.

In another preferred embodiment of the present invention, the sample flow control ports allow the first solvent to flow out at a rate of 0.5 to 10 μl/min to regulate the flow rate of the sample into the first and second solid-phase extraction columns.

In another preferred embodiment of the present invention, the sample storage loop has a volume of 1 to 10 μl and allows the amount of the sample loaded exceeding the upper volume limit to flow out to waste through the sample outlet port.

In another preferred embodiment of the present invention, each of the first and second reverse-phase liquid chromatography columns has a diameter of 15 to 150 μm and a length of 10 to 150 cm.

In another preferred embodiment of the present invention, the first and second reverse-phase liquid chromatography columns are connected to a mass spectrometer.

In still another preferred embodiment of the present invention, the direction of the first solvent flowing into the first or second solid-phase extraction column in a sample introduction mode is opposite to that of the mixed solvent flowing into the first or second solid-phase extraction column in a sample separation mode.

DESCRIPTION OF THE PREFERRED EMBODIMENTS

Preferred embodiments of the present invention will now be described in greater detail with reference to the accompanying drawings.

The present invention provides an ultrahigh-pressure DO-SPE/cRPLC system comprising: a sample loading valve into which a first solvent and a sample to be analyzed are loaded; a first column valve in flow communication with a first solid-phase extraction column and a first reverse-phase liquid chromatography column; a second column valve in flow communication with a second solid-phase extraction column and a second reverse-phase liquid chromatography column; a column-switching valve for determining whether the sample is transferred to either the first column valve or the second column valve; a solvent selection valve in flow communication with the first and second column valves to supply the first solvent or a mixed solvent of the first solvent and a second solvent to the first and second column valves; a second solvent loading valve, in flow communication with a solvent mixer, into which the first and second solvents are loaded; a supply pump for loading the second solvent into the second solvent loading valve; and a supply pump for loading the first solvent into the sample loading valve, the second solvent loading valve and the solvent selection valve.

Figure 1A:
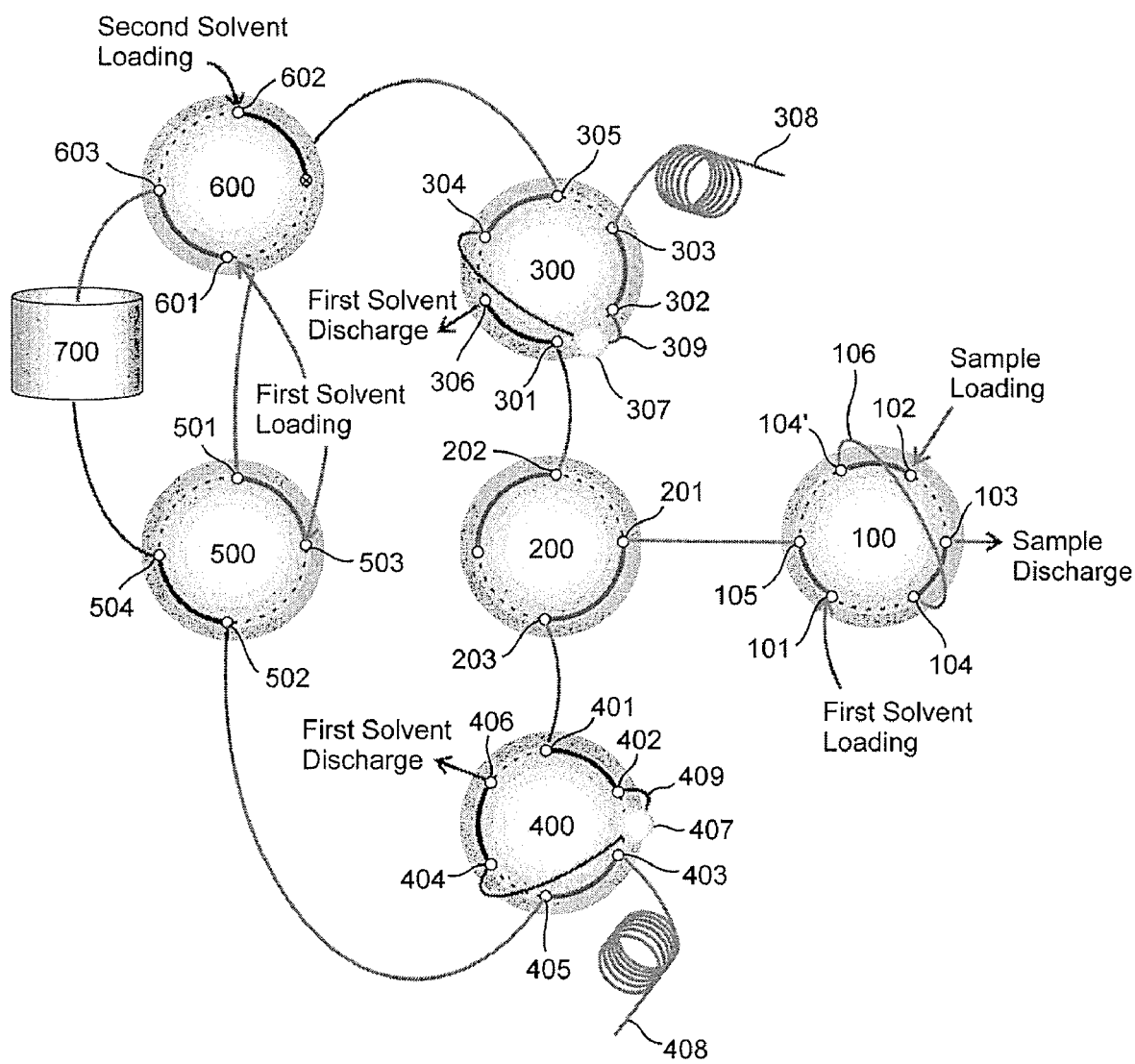
FIG. 1a is a diagram schematically illustrating the connection of valves at the initial stage of sample injection in the system of the present invention.

As shown in FIG. 1a, the ultrahigh-pressure DO-SPE/cRPLC system of the present invention comprises six valves, i.e. a sample loading valve 100, a column-switching valve 200, a first column valve 300, a second column valve 400, a solvent selection valve 500, and a second solvent loading valve 600.

A sample to be analyzed is loaded into the sample loading valve 100. The sample loading valve 100 includes six ports: a port 101 into which the first solvent is introduced (hereinafter, referred to as a 'first solvent introduction port'), a port 102 into which the sample is introduced (hereinafter, referred to as a 'sample introduction port'), a port 103 through which an excess amount of the sample flows out to waste (hereinafter, referred to as a 'sample outlet port'), ports 104 and 104' to which a sample storage loop is connected (hereinafter, referred to as 'sample storage loop connection ports'), and a port 105 to which the column-switching valve is connected (hereinafter, referred to as a 'column-switching valve connection port').

First, a sample is loaded into the sample loading valve through the sample introduction port 102 and is connected to a sample storage loop 106 having a predetermined volume. This connection enables enrichment of the sample through multiple injections when a user determines that the concentration of the sample is too low.

The sample storage loop 106 preferably has a volume of 1 to 10 µl. The use of the sample storage loop 106 having a volume of less than 1 µl makes the sample difficult to handle. Meanwhile, the use of the sample storage loop 106 having a volume of more than 10 µl unfavorably prolongs the time needed for sample injection.

The sample loading valve 100 is provided with the sample outlet port 103. The sample outlet port 103 plays a role in allowing an excess amount of the sample to flow out to waste therethrough so that the sample can be received within the sample storage loop.

Figure 1B:
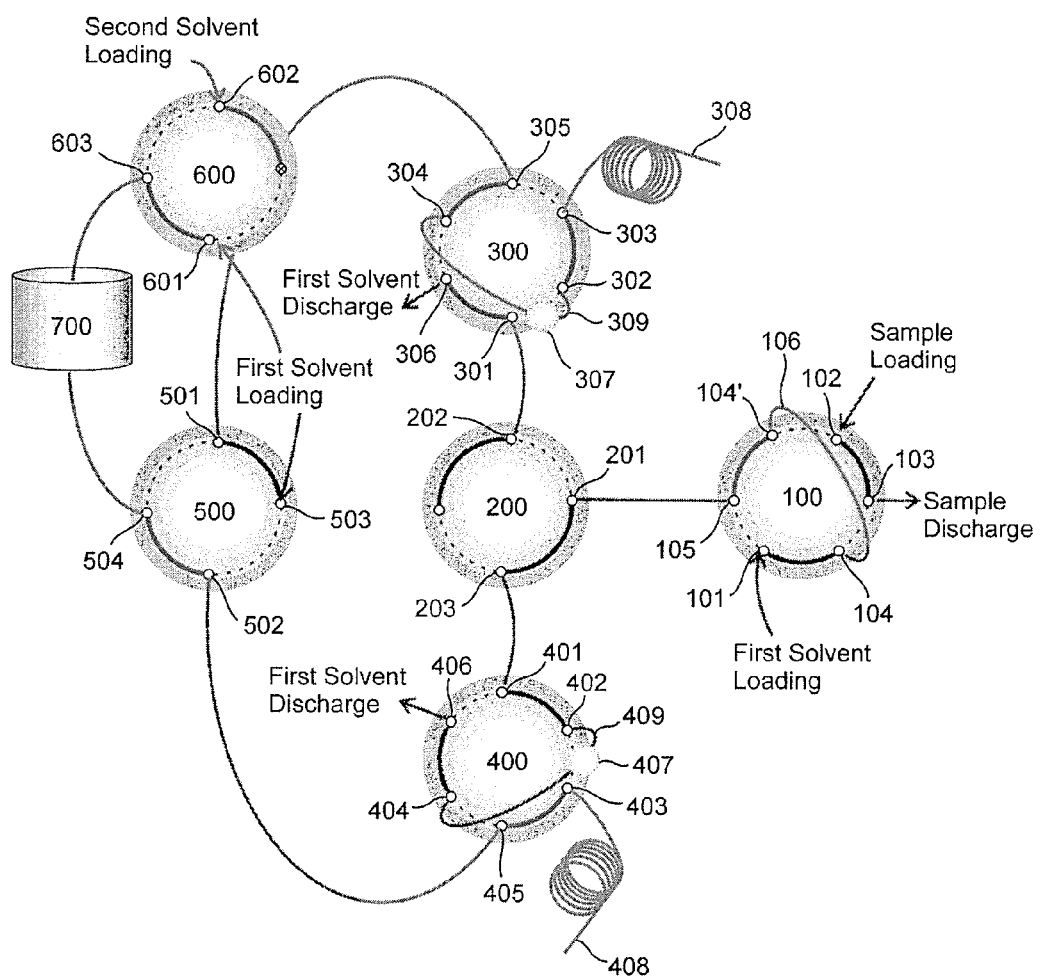
FIG. 1b is a diagram schematically illustrating the connection of valves at the time when a sample loading valve is switched from a sample introduction mode to an analysis mode in the system of the present invention.

After completion of the sample loading, a mode conversion switch (not shown) of the sample loading valve 100 is set to switch the connection of the ports from the sample introduction mode to an analysis mode. This mode switching is shown in FIG. 1*b*.

In the analysis mode, the first solvent is loaded into the sample loading valve 100 through the first solvent introduction port 101 by means of the first solvent supply pump (not shown). The sample is transferred to the column-switching valve 200 through the sample storage loop connection ports 104 and 104' by the hydraulic pressure of the first solvent. Referring to FIGS. 1*a* and 1*b*, the solvent selection valve 500 and the second solvent loading valve 600 are provided with first solvent introduction ports 503 and 601, respectively. The first solvent supply pump supplies the first solvent to the sample loading valve 100, the solvent selection valve 500 and the second solvent loading valve 600 through the first solvent introduction ports 101, 503 and 601, respectively.

It is preferred that the first solvent be loaded at a pressure of 5,000 into 20,000 psi through the first solvent introduction ports 101, 503 and 601 by means of the first solvent supply pump. The supply of the first solvent at a pressure lower than 5,000 psi limits the length of the columns used, resulting in a decrease in separation resolution. Meanwhile, the supply of the first solvent at a pressure higher than 20,000 psi offers the possibility of leakage of the solvent from the valves.

A determination is made as to whether the sample introduced into the column selection valve 200 through the column-switching valve connection port 105 flows into the first column valve 300 or the second column valve 400. The column-switching valve 200 includes a port 201 to which the sample loading valve is connected (hereinafter, referred to as a 'sample loading valve connection port'), a port 202 to which the first column valve is connected (hereinafter, referred to as a 'first column valve connection port'), and a port 203 to which the second column valve is connected (hereinafter, referred to as a 'second column valve connection port').

For example, the flowing of the sample into the second column valve 400 is shown in FIG. 1*b*. In this case, the sample introduced through the sample loading valve connection port 201 is transferred to the second column valve 400 through the second column valve connection port 203.

The second column valve 400 includes a port 401 to which the column-switching valve is connected (hereinafter, referred to as a 'column-switching valve connection port'), a port 402 to which a second solid-phase extraction column 409 is connected (hereinafter, referred to as a 'second solid-phase extraction column connection port'), a port 403 to which the second reverse-phase liquid chromatography column is connected (hereinafter, referred to as a 'second reverse-phase liquid chromatography column connection port'), a port 404 to which a solvent flow splitter is connected (hereinafter, referred to as a 'solvent flow splitter connection port'), a port 405 to which the solvent selection valve is connected (hereinafter, referred to as a 'solvent selection valve connection port'), and a sample flow control port 406.

The sample transferred from the column-switching valve 200 sequentially passes through the column-switching valve connection port 401 and the second solid-phase extraction column connection port 402 to reach the second solid-phase extraction column 409. The second solid-phase extraction column 409 is coupled directly to the second solid-phase extraction column connection port 402. Each of the first and second solid-phase extraction columns 309 and 409 has a diameter of 50 to 500 µm and a length of 1 to 4 cm. The lengths of the extraction columns 309 and 409 are much shorter than existing solid-phase extraction columns. The use of the shorter solid-phase extraction columns in the system of the present invention achieves maximized separation resolution of the sample despite high operating pressure (ca. 20,000 psi). As will be explained below, the direction of the sample introduced in the sample introduction mode is opposite to that of the sample separated in a sample separation mode, thus achieving further improved separation resolution of the sample.

In the system of the present invention, each of the solid-phase extraction columns 309 and 409 is separated from each of the reverse-phase liquid chromatography columns 308 and 408 by a separation column and a channel installed within a switch valve only. Therefore, the columns can be interconnected together even with a very small dead volume. That is, the total dead volume of the system according to the present invention is determined by channels installed between the solid-phase extraction column connection ports 302 and 402 and the reverse-phase liquid chromatography column connection ports 303 and 403. The system of the present invention uses a nanobore switch valve to connect the columns so that the dead volume can be minimized.

Each of the solid-phase extraction columns 309 and 409 uses a stainless steel liner as an internal inducer and is packed with a packing material (e.g., C18).

Stainless steel screens (2 µm pore) are attached to both ends of the liner to prevent the packing material from escaping from the column. With this configuration, the solid-phase extraction columns are sufficiently strong to withstand high pressures.

On the other hand, the flow rate of the sample introduced into the second solid-phase extraction column 409 by the hydraulic pressure of the first solvent is regulated by the sample flow control port 406. The sample flow control port 406 allows the first solvent to flow out at a rate of 0.5 to 10 µl/min to regulate the flow rate of the sample into the second solid-phase extraction column 409. The sample flow control ports 306 and 406 also allow salt ingredients contained in the sample to flow out, thus achieving efficient desalting.

A sample flow rate control column (not shown) is connected to each of the sample flow control ports 306 and 406. For example, the sample flow rate control column is a stainless steel tube packed with a packing material (e.g., C18). The sample flowing through the sample flow control port 306 or 406 passes through the sample flow rate control column. Through this process, the flow rate of the sample is regulated.

To sum up, a certain amount of the sample is filled in the sample storage loop 106 through the sample introduction port 102, transferred to the column-switching valve 200 by the first solvent introduced through the first solvent introduction port 101, transferred to the second column valve 400, and loaded into the second solid-phase extraction column 409.

Next, the sample loaded into the second solid-phase extraction column 409 is separated using a second solvent, and an explanation thereof will be given below.

Particularly, as will be explained below, the direction of the first solvent flowing into the first or second solid-phase extraction column in the sample introduction mode is opposite to that of the mixed solvent flowing into the first or second solid-phase extraction column in a sample separation mode, thus achieving further improved separation resolution of the sample.

The first solvent functions to load the sample into the solid-phase extraction columns 309 and 409 and to equilibrate one of the columns that is not involved in the separation of the sample during alternating operation of the columns. The second solvent is responsible for the separation of the sample in the solid-phase extraction columns 309 and 409. To initiate the separation of the sample by the second solvent, a mode conversion switch (not shown) of the second column valve 400 is set to switch from the sample introduction mode to a sample separation mode.

Figure 1C:
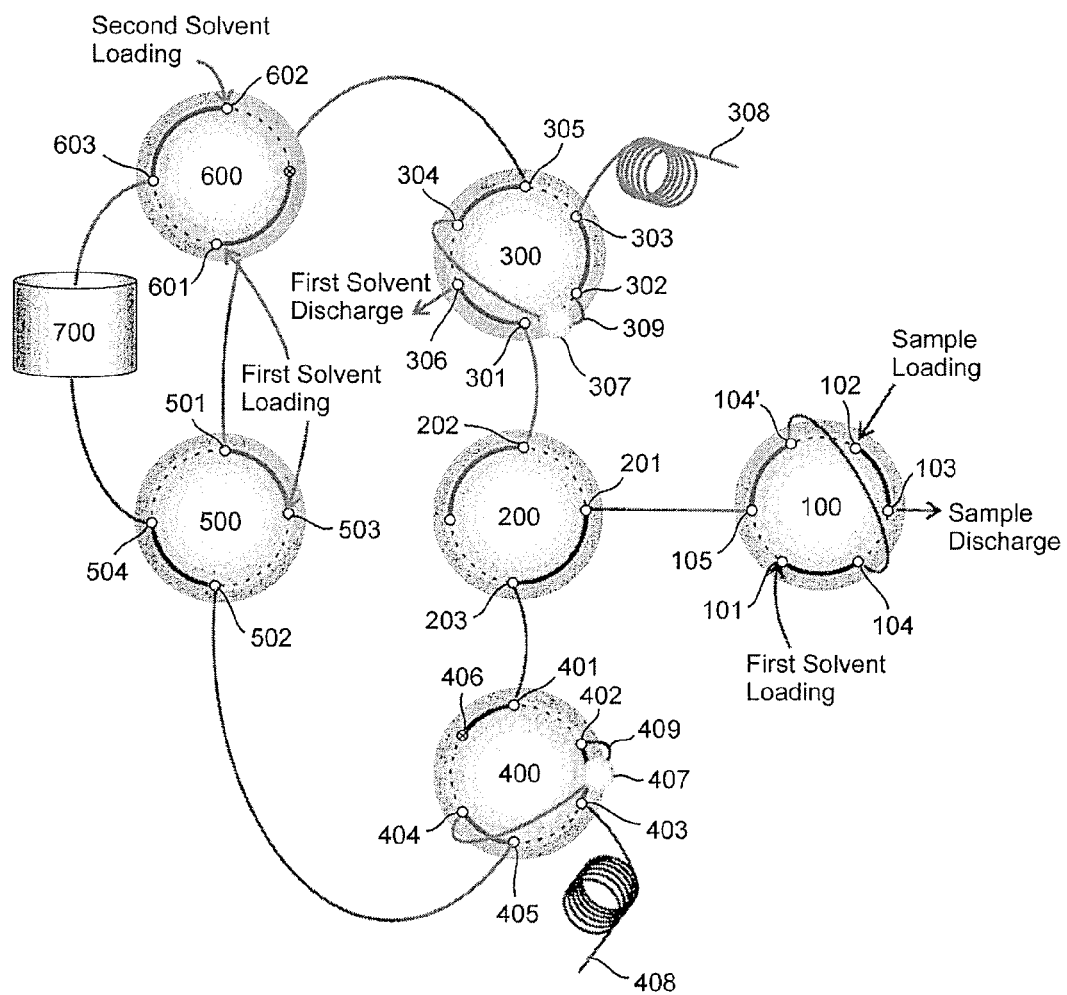
FIG. 1c is a diagram schematically illustrating the connection of valves at the time when a second column valve is switched to a sample separation mode in the system of the present invention.

FIG. 1c shows a state where the second column valve 400 is switched to a sample separation mode. In the sample separation mode shown in FIG. 1c, the second solid-phase extraction column 409 is connected directly to the second reverse-phase liquid chromatography column 408, and a mixed solvent of the first and second solvents sequentially passes through the solvent flow splitter connection port 404 and a solvent flow splitter 407 to reach the second solid-phase extraction column 409 and the second reverse-phase liquid chromatography column 408.

In the meanwhile, the second solvent is introduced into the second solvent loading valve 600 through a port 602 into which the second solvent is introduced (hereinafter, referred to as a 'second solvent introduction port'), transferred to the solvent mixer 700 via a port 603 to which the solvent mixer is connected (hereinafter, referred to as a 'solvent mixer connection port') by switching of a switch (not shown) provided in the second solvent loading valve 600, mixed with the first solvent in the solvent mixer, and transferred to the second column valve 400 through a port 504 into which the mixed solvent is introduced (hereinafter, referred to as a 'mixed solvent introduction port') and a port 502 to which the second column valve is connected (hereinafter, referred to as a 'second column valve connection port').

The solvent flow splitter 407 is connected to a 'T'-shaped solvent separation column to divide the solvent flow. A large portion (15-20 μ/min.) of the mixed solvent is allowed to flow out through the solvent flow splitter 407 to generate a solvent gradient and the remaining portion of the mixed solvent is transferred to the second column valve 400.

The sample is separated in the second solid-phase extraction column 409 by varying the ratio between the first and second solvents introduced through the solvent selection valve connection port 405 as a function of time. That is, as the proportion of the second solvent in the mixed solvent increases, the degree of dissociation of the sample bound to the solid-phase extraction column increases. The sample undergoing dissociation is loaded into the second reverse-phase liquid chromatography column 408 where the sample is separated.

Various combinations of solvents may be selected, without limitation, as the first and second solvents. For example, a solvent containing 0.05% trifluoroacetic acid and 0.2% acetic acid in water may be used as the first solvent, and a solvent containing 0.1% trifluoroacetic acid and 90% acetonitrile in water may be used as the second solvent. That is, the solvent combination employs a system in which the degree of dissociation of the sample bound to the solid-phase extraction column increases with increasing amount of the acetonitrile in the solvents.

On the other hand, the proportion of the second solvent in the mixed solvent introduced through the solvent selection valve connection port 405 increases with time. The proportion of the first solvent approaches 100% at the initial stage of switching of the mode conversion switch (not shown) of the second column valve 400 from the sample introduction mode to the sample separation mode, whereas the proportion of the second solvent approximates 100% at the end of the sample separation. The proportion of the second solvent in the mixed solvent may be increased by switching the second solvent loading valve 600 from the closed mode to the opened mode, which allows the second solvent to flow out, to increase the amount of the second solvent transferred to the solvent selection valve 500.

The second solvent is introduced at a pressure of 5,000 to 20,000 psi into the second solvent introduction port 602 of the second solvent loading valve 600 by means of the second solvent supply pump (not shown). The first solvent is supplied from the first solvent supply pump (not shown) to the second solvent loading valve 600 through the first solvent introduction port 601. The introduced first and second solvents are transferred to the solvent mixer 700 through the solvent mixer connection port 603. The first and second solvents introduced from the second solvent loading valve 600 are mixed together in a predetermined ratio in the solvent mixer 700, and then the mixed solvent is transferred to the solvent selection valve 500.

A determination is made as to whether the mixed solvent introduced through the mixed solvent introduction port 504 is transferred from the solvent selection valve 500 to the first column valve 300 or the second column valve 400. For example, FIG. 1c shows a state where the second column valve 400 is in a separation mode, and therefore, the mode of the solvent selection valve 500 is switched such that the mixed solvent can be transferred to the second column valve 400. In this case, the mixed solvent sequentially passes through the second column valve connection port 502 of the solvent selection valve 500, the solvent introduction port 405 of the second column valve 400 and the solvent flow splitter 407 to reach the second solid-phase extraction column 409 and the second reverse-phase liquid chromatography column 408.

Each of the first and second reverse-phase liquid chromatography columns 308 and 408, where the sample is separated, preferably has a diameter of 15 to 150 μm and a length of 10 to 150 cm. The first and second reverse-phase liquid chromatography columns 308 and 408 are connected to a mass spectrometer, where subsequent analysis steps can be conducted.

On the other hand, the use of the first and second column valves 300 and 400 in the system of the present invention enables one of the columns to be equilibrated while the sample is separated in the other column. In addition, immediately after the sample separation is completed in one column, the other column is ready for sample separation. According to this process, for example, the first column is equilibrated while the sample is separated in the second column, and after completion of the sample separation in the second column, the sample separation is performed in the first column, so that the sample separation can be performed in a consecutive manner. Referring again to FIG. 1a, while the sample is separated in the second column, the first solvent loaded by means of the first solvent supply pump sequentially passes through the first solvent introduction port 503 of the solvent selection valve 500 and the first column valve connection port 501 to reach the first column valve 300, where the first column is ready for equilibration.

Thereafter, the sample analysis and the equilibration are conducted in the first and second columns, respectively. This process is performed in the same manner as in the former process illustrated in FIGS. 1a to 1c, except that the first and second columns alternate with each other.

Hereinafter, the present invention will be explained in more detail with reference to the following examples. However, these examples are not to be construed as limiting the scope of the invention.

EXAMPLES

Pretreatment of Samples

Enolase from bakers' yeast, which was purchased from Sigma-Aldrich (St. Louis, Mo., USA), was used as a sample. The sample was pretreated with sequence-grade modified porcine trypsin from Promega (Madison, Wis., USA) in accordance with the following procedure.

The enolase was dissolved in 100 mM $NH_4HCO_3$ buffer, denatured thermally at 90° C. for 10 min. After cooling to room temperature, methanol was added and then trypsin was added with the final substrate-to-enzyme mass ratio of 50:1. Tryptic digestion proceeded for 15 h at 37° C.

Tryptic peptides of whole yeast lysates were used to investigate the applicability of using the DO-SPE/cRPLC system to analyze complex proteome samples. Yeast proteomes were obtained by cell lysis of S. cerevisiae haploid strains Y2805 (MATa pep::his3 prb1-D1.6R can1 his1-200 ura3-52) and AF-2 (HMLa or HMRa ho ade2-1 trp1-1 can1-100 leu2-3, 112 his3-11, 15 ura3-1 ssd1) according to the procedure described in Kim, M.-S., Choie, W.-S., Shin, Y. S., Yu, M. H., Lee, S.-W., Bull. Korean Chem. Soc. 2004, 25, 1833-1839. After the proteins were dissolved in the 100 mM $NH_4HCO_3$ buffer, trypsin was added, and digestion proceeded for 24 h at 37° C. The resulting peptides were dried completely using a SpeedVac system (SPD1010; ThermoSavant, Holbrook, N.Y., USA) and then stored at −20° C. until required for further experiments.

Materials and Instruments

A solvent containing 0.05% trifluoroacetic acid (commercially available from Sigma-Aldrich, St. Louis, Mo., USA) and 0.2% acetic acid in water was used as a first solvent, and a solvent containing 90% acetonitrile (commercially available from J. T. Baker, Phillipsburg, N.J., USA) and 0.1% trifluoroacetic acid in water was used as a second solvent.

Capillary columns (75 µm (ID)×360 µm (OD) 1 m (length)), i.e. reverse-phase liquid chromatography columns, were manufactured in-house through slurry packing of a fused-silica capillary with C18-bonded particles, as described in Shen, Y., Moore, R. J., Zhao, R., Blonder, J., et al., Anal. Chem. 2003, 75, 3596-3605; Shen, Y., Tolic N., Masselon, C., Pasa-Tolic L. et al., Anal. Chem. 2004, 76, 144-154; Shen, Y., Smith, R. D., Unger K. K., Kumar, D., Lubda, D., Anal. Chem. 2005, 77, 6692-6701).

A solid-phase extraction column was prepared using an internal reducer obtained from VICI (Houston, Tex., USA). A 1-cm liner (250 µm ID), placed inside of the internal reducer (1/16" to 1/32"), was packed with the C18 material at a pressure of 10,000 psi. Once the packing step was complete, the columns were subjected to sonication for 5 min while maintaining the pressure at 10,000 psi and the pressure was then slowly released overnight before using the column to prevent the packed C18 materials from dispersing. Stainless-steel screens (2 µm pore) were attached to both ends of the liner before they were used in experiments. To investigate the effect of the SPE column length on the LC separation efficiency, a 3.5-cm-long SPE column was manufactured by packing a 3.5-cm-long piece of stainless-steel tubing (250 µm ID) with the same C18 materials.

A 7-tesla Fourier-transform ion cyclotron resonance mass spectrometer (FTICR, LTQ-FT, ThermoFinnigan) equipped with a home-built nanoelectrospray ionization interface was connected to the first and second reverse-phase liquid chromatography columns.

Evaluation of Analytical Results

1) High Efficiency of the On-Line Solid-Phase Extraction (SPE) Column

The tryptic enolase digests were analyzed using the system of the present invention to investigate the efficiency of the on-line SPE column.

Figure 2A:
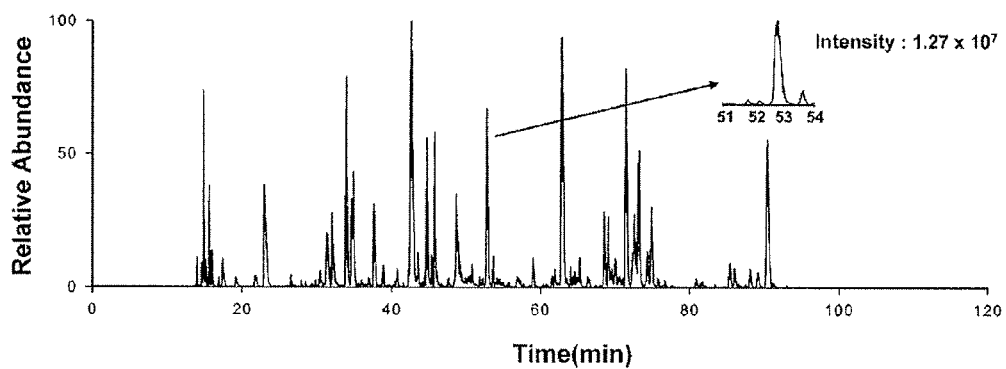
FIG. 2a is a chromatogram obtained when 0.2 μg of a sample was analyzed on the system of the present invention.
Figure 2B:
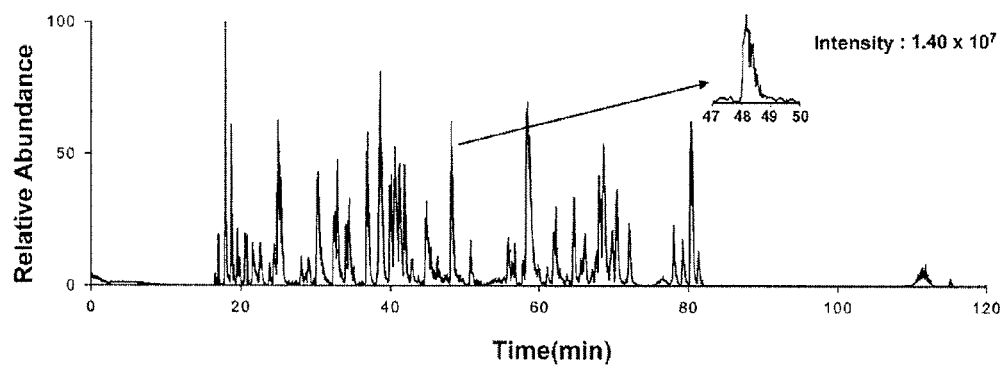
FIG. 2b is a chromatogram obtained when 1 μg of a sample was analyzed on a dual column system without using a solid-phase extraction column.

FIG. 2a is a chromatogram obtained when 0.2 µg of the sample was analyzed on the system of the present invention, and FIG. 2b is a chromatogram obtained when 1 µg of a sample was analyzed on a dual column system without using a solid-phase extraction column. In both systems, the operating pressure was 10,000 psi and the solvent flow rate within the 1-m-long and 75-mm-ID capillary column was ca. 0.3 mL/min. The chromatograms demonstrate the increased separation resolution obtained when using the on-line SPE column. Although a smaller amount of the sample was injected, the DO-SPE/cRPLC system provided a chromatographic peak intensity ($1.40 \times 10^7$) higher than that obtained when using the LC system without an SPE column ($1.27 \times 10^7$). The similar chromatographic peaks observed in the chromatograms obtained from both LC systems (i.e., with and without an SPE column) confirm that the sample loss caused by the SPE was negligible at most.

Figure 3A:
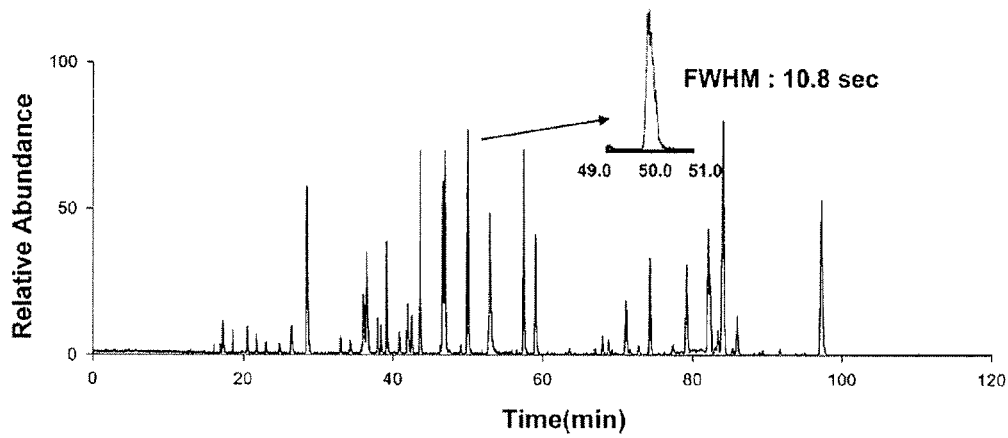
FIGS. 3a and 3b provide a comparison of chromatograms obtained using 3.5-cm-long and 1-cm-long solid-phase extraction columns in the system of the present invention, respectively.
Figure 3B:
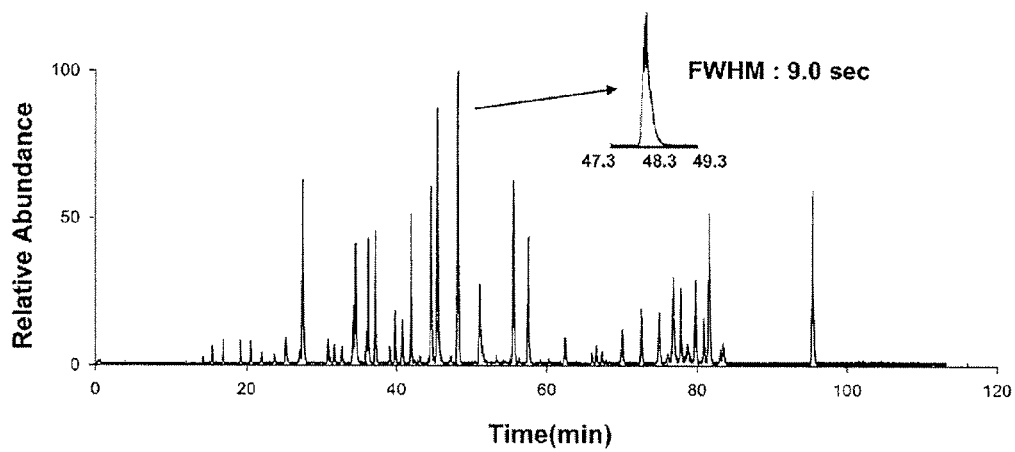

FIG. 3 provides a comparison of the chromatograms obtained from the LC systems utilizing (A) 3.5-cm-long and (B) 1-cm-long SPE columns. It has been noted previously that the efficiency of SPE/capillary LC should increase when the length of SPE column is decreased, mainly because the pressure drop across the SPE column is inversely proportional to the ratio of the lengths of the LC columns and SPE columns. As mentioned above, the length of the SPE column could be reduced to 1 cm. In addition, the SPE column could be operated at the pressures as high as 20,000 psi without damage to the system or sample leakage. While some short SPE columns (as short as 1 mm in length) are commercially available, they are to be used at the conventional LC operating pressures (<5000 psi) and, thereby, they are usually coupled to a relatively short LC column. The chromatograms of FIGS. 3a and 3b show that the peak width was improved when the shorter SPE column was used.

2) On-Line Sample Enrichment Through Multiple Injections

When the user determines that the concentration of the sample is too low, the sample loaded into the sample storage loop can be enriched in the solid-phase extraction column before the separation of the sample. As explained earlier, the sample loading valve is switched to allow the sample to be loaded into and enriched in the solid-phase extraction column through multiple injections while maintaining the column valve in a sample introduction mode, and then the column valve is switched to a sample separation mode.

Figure 4A:
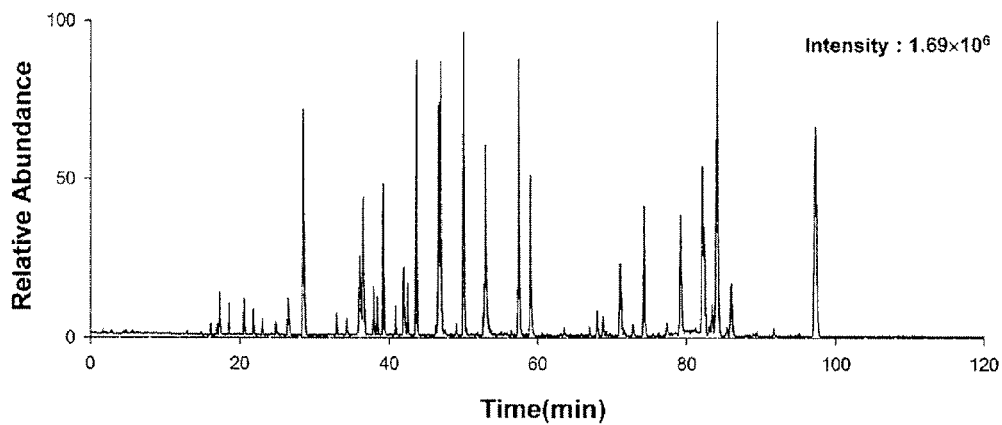
FIGS. 4a and 4b are chromatograms obtained after a single injection of 50 ng of enolase peptides and five injections, each of 10 ng, of the same sample into the system of the present invention, respectively.
Figure 4B:
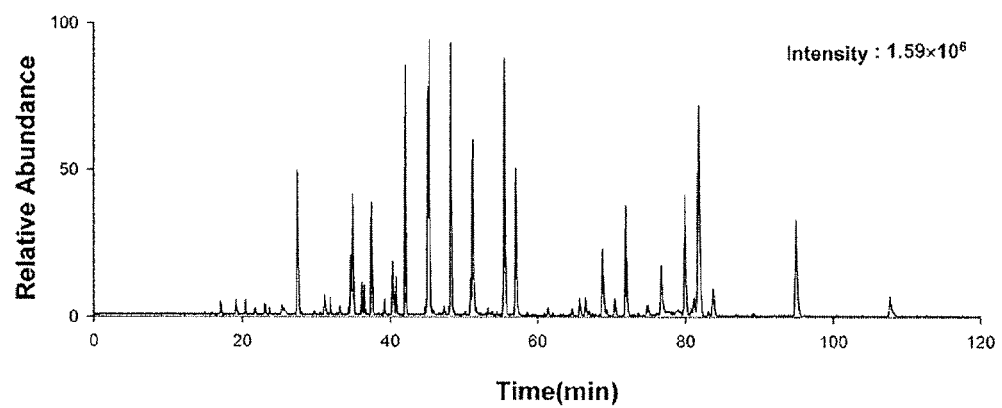

FIGS. 4a and 4b are chromatograms obtained after a single injection of 50 ng of enolase peptides and five injections, each of 10 ng, of the same sample, respectively. The peak intensities and retention times in these chromatograms are nearly identical, indicating that negligible sample loss was caused despite the multiple injections.

3) Efficient Removal of Salts

Figure 5A:
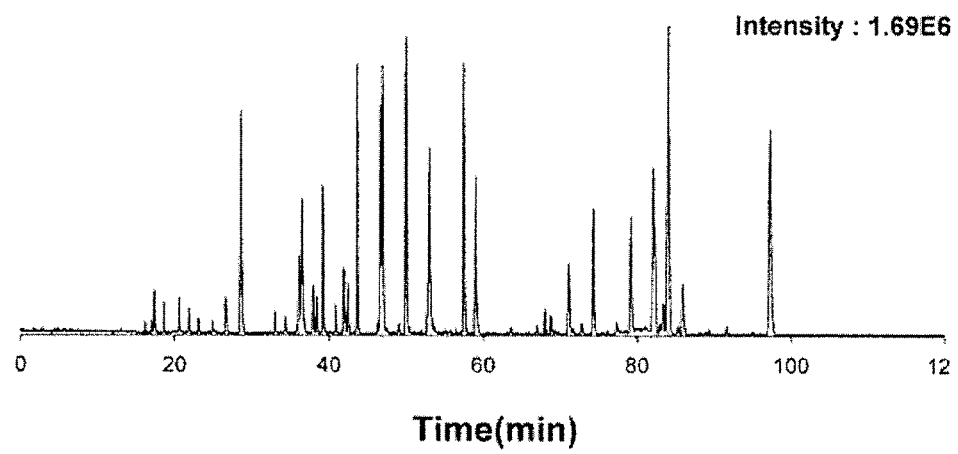
FIG. 5a is a chromatogram of 50 ng of desalted enolase peptides.
Figure 5B:
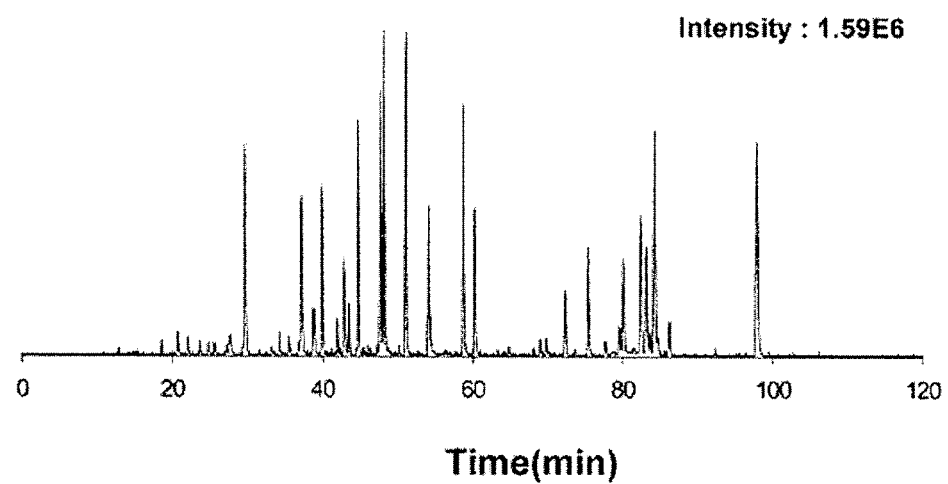
FIGS. 5b and 5c are chromatograms obtained after 50 ng of enolase peptides in 8M urea were injected into the system of the present invention, followed by operation for 1.5 and 5 minutes, respectively.
Figure 5C:
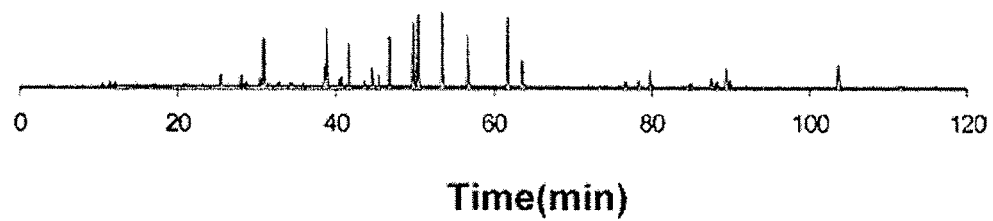
Figure 6A:
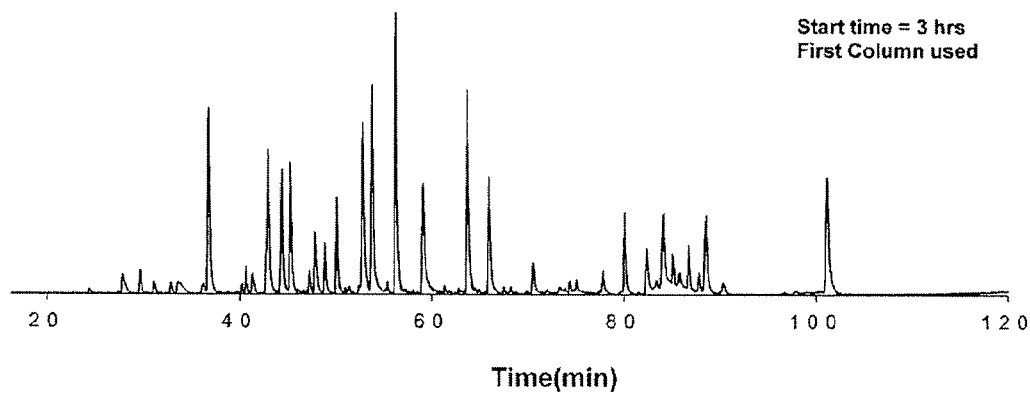
FIGS. 6a, 6b, 6c and 6d are chromatograms obtained from four consecutive experiments using the system of the present invention in which the time required for column washing/solvent exchange/solvent stabilization and the time of use of columns for each experiment were set to 30 minutes and 2 hours, respectively.
Figure 6B:
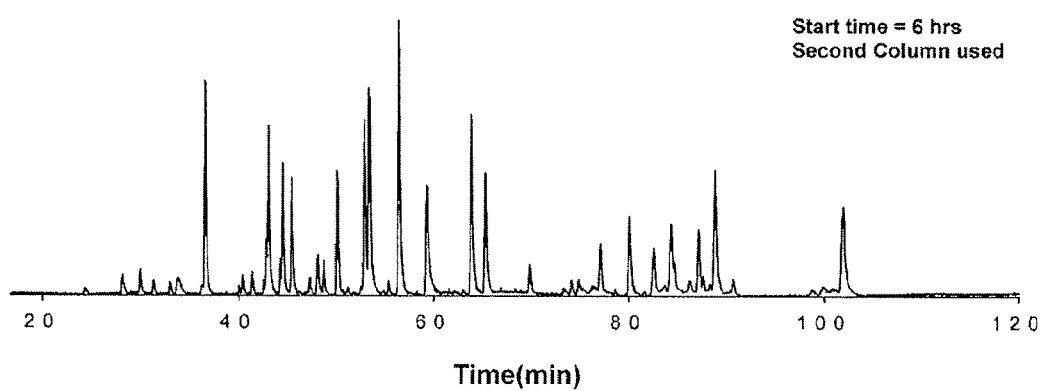
Figure 6C:
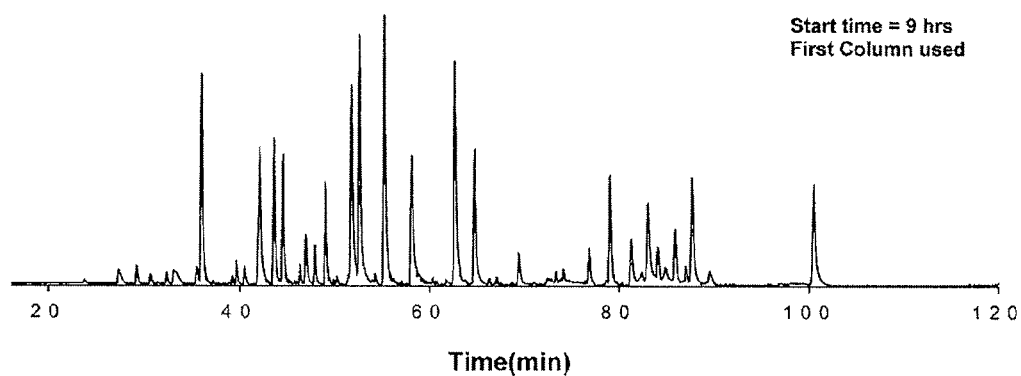
Figure 6D:
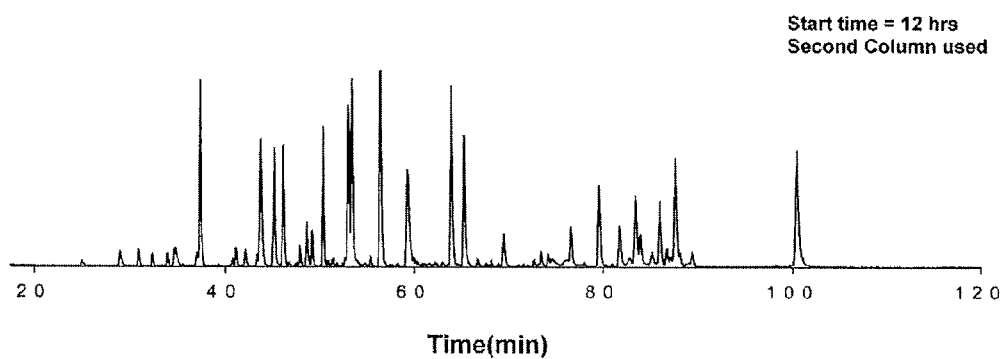

The desalting capability of the system of the present invention was analyzed. FIG. 5a is a chromatogram of 50 ng of desalted enolase peptides. FIGS. 5b and 5c are chromatograms obtained after 50 ng of enolase peptides in 8 M urea were injected into the system, followed by operation for 1.5 and 5 min., respectively.

The peak intensities shown in FIG. 5b are slightly lower because 1.5 min was not a sufficiently long time for the removal of the urea salt; after 5 min of desalting, however, the resulting chromatogram (FIG. 5c) is very similar to the one obtained when no urea was added to the sample (FIG. 5a). This finding demonstrates that the on-line SPE/cRPLC system can provide an efficient desalting when the injection time is controlled carefully.

4) Minimization of Column Equilibration Time

The system of the present invention has an advantage in that the column equilibration time between successive experiments can be minimized. For example, 1-m-long and 75-mm-ID capillary LC columns require a practical equilibration time of ca. 2 h and a solvent exchange/stabilization time of ca. 0.5 hours before subsequent experimentation. In contrast, the system of the present invention essentially removes the equilibration time and requires ca. 0.5 hours for solvent exchange/stabilization to reduce the possibility of occurrence of contaminants in the column to almost zero.

FIGS. 6a, 6b, 6c and 6d are chromatograms obtained from four consecutive experiments using the system of the present invention in which the time required for column washing/solvent exchange/solvent stabilization and the time of use of columns for each experiment were set to 30 minutes and 2 hours, respectively. As indicated in FIGS. 6a-6d, only slight changes appeared in the retention times and intensities of the peaks in the four chromatograms. The system of the present invention required a total of 10 hours (i.e. the time of use of columns: 8 hours+the time required for equilibration and solvent exchange/stabilization: 10 hours) for the four experiments, whereas a typical SPE/cRPLC system requires a total of 18 hours (i.e. the time of use of columns: 8 hours+the time required for equilibration and solvent exchange/stabilization: 10 hours) to complete the same set of experiments, demonstrating that the system of the present invention showed better analytical results.

5) Analysis of Complex Proteome Samples

The tryptic peptides of whole yeast lysates were used to demonstrate the applicability of the system according to the present invention to highly complex proteomes.

Figure 7A:
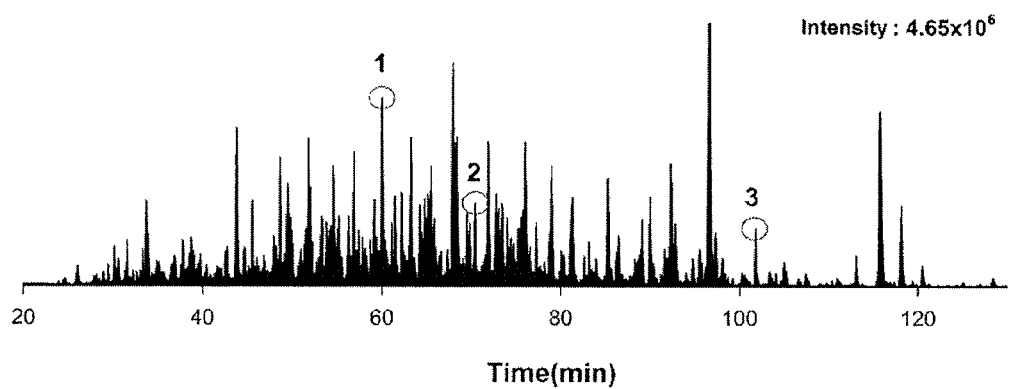
FIGS. 7a and 7b are chromatograms obtained after injection of tryptic peptides (5 ng and 10 ng, respectively) of whole yeast lysates.
Figure 7B:
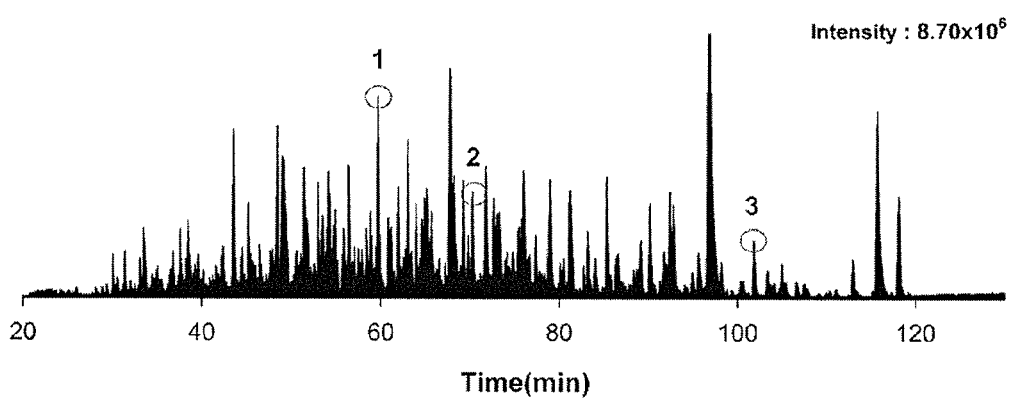

FIGS. 7a and 7b are chromatograms obtained after injection of the tryptic peptides (5 ng and 10 ng, respectively) of whole yeast lysates. The chromatograms of FIGS. 7a and 7b indicate that the peaks were sharp and well-defined with only slight differences in their retention times (<0.5%). It is clear from the results that the complex samples were very effectively separated in the system of the present invention.

As apparent from the above description, the ultrahigh-pressure DO-SPE/cRPLC system of the present invention requires minimal time (i.e. dead time) for column equilibration between successive experiments to shorten the total time required for the experiments by a factor of about two. In addition, the system of the present invention enables rapid sample injection, on-line sample desalting and sample enrichment. Furthermore, the system of the present invention is highly reproducible in terms of liquid chromatography (LC) retention time and can be operated at a pressure as high as 10,000 psi.

What is claimed is:

1. An ultrahigh-pressure dual on-line solid phase extraction/capillary reverse-phase liquid chromatography (DO-SPE/cRPLC) system comprising:
   a sample loading valve into which a first solvent and a sample to be analyzed are loaded;
   a first column valve in flow communication with a first solid-phase extraction column and a first reverse-phase liquid chromatography column;
   a second column valve in flow communication with a second solid-phase extraction column and a second reverse-phase liquid chromatography column;
   a column-switching valve for determining whether the sample is transferred to either the first column valve or the second column valve;
   a solvent selection valve in flow communication with the first and second column valves to supply the first solvent or a mixed solvent of the first solvent and a second solvent to the first and second column valves;
   a second solvent loading valve, in flow communication with a solvent mixer, into which the first and second solvents are loaded;
   a supply pump for loading the second solvent into the second solvent loading valve; and
   a supply pump for loading the first solvent into the sample loading valve, the second solvent loading valve and the solvent selection valve.

2. The system according to claim 1, wherein the column-switching valve includes a sample loading valve connection port, a first column valve connection port, and a second column valve connection port.

3. The system according to claim 1, wherein the second column valve includes a column-switching valve connection port, a second solid-phase extraction column connection port, a second reverse-phase liquid chromatography column connection port, a solvent flow splitter connection port, a solvent selection valve connection port, and a sample flow control port.

4. The system according to claim 1, wherein the solvent selection valve includes a first column valve connection port, a second column valve connection port, a first solvent introduction port, and a mixed solvent introduction port.

5. The system according to claim 1, wherein the second solvent loading valve includes a first solvent introduction port, a second solvent introduction port, and a solvent mixer connection port.

6. The system according to claim 1, wherein the first solvent is loaded at a pressure of 5,000 to 20,000 psi by means of the first solvent supply pump.

7. The system according to claim 1, wherein the second solvent is loaded at a pressure of 5,000 to 20,000 psi by means of the second solvent supply pump.

8. The system according to claim 1, wherein each of the first and second solid-phase extraction columns has a diameter of 50 to 500 μm and a length of 1 to 4 cm.

9. The system according to claim 1, wherein each of the first and second reverse-phase liquid chromatography columns has a diameter of 15 to 150 μm and a length of 10 to 150 cm.

10. The system according to claim 1, wherein the first and second reverse-phase liquid chromatography columns are connected to a mass spectrometer.

11. The system according to claim 1, wherein the direction of the first solvent flowing into the first or second solid-phase extraction column in a sample introduction mode is opposite to that of the mixed solvent flowing into the first or second solid-phase extraction column in a sample separation mode.

12. The system according to claim 1, wherein the sample loading valve includes a first solvent introduction port, a sample introduction port, a sample outlet port, sample storage loop connection ports, and a column-switching valve connection.

13. The system according to claim 12, wherein the sample storage loop has a volume of 1 to 10 μl and allows the amount of the sample loaded exceeding the upper volume limit to flow out to waste through the sample outlet port.

14. The system according to claim 1, wherein the first column valve includes a column-switching valve connection port, a first solid-phase extraction column connection port, a first reverse-phase liquid chromatography column connection port, a solvent flow splitter connection port, a solvent selection valve connection port, and a sample flow control port.

15. The system according to claim 14, wherein the solvent flow splitter is connected to a 'T'-shaped solvent separation column to divide the solvent flow, and the solvent separation column allows the mixed solvent to flow out at a rate of 15 to 20 μl/min to generate a solvent gradient and serves to transfer only the remaining portion of the mixed solvent to the first and second column valves.

16. The system according to claim 14, wherein the sample flow control ports allow the first solvent to flow out at a rate of 0.5 to 10 μl/min to regulate the flow rate of the sample into the first and second solid-phase extraction columns.

* * * * *